(12) United States Patent
Funnell

(10) Patent No.: US 9,089,345 B2
(45) Date of Patent: Jul. 28, 2015

(54) RONGEUR WITH VENTED T-SLIDE AND/OR INCREASED STRENGTH

(76) Inventor: David M. Funnell, Medford, MA (US)

( * ) Notice: Subject to any disclaimer, the term of this patent is extended or adjusted under 35 U.S.C. 154(b) by 80 days.

(21) Appl. No.: 13/562,120

(22) Filed: Jul. 30, 2012

(65) Prior Publication Data

US 2013/0041378 A1 Feb. 14, 2013

Related U.S. Application Data

(60) Provisional application No. 61/574,098, filed on Jul. 28, 2011, provisional application No. 61/626,283, filed on Sep. 26, 2011, provisional application No. 61/630,693, filed on Dec. 19, 2011.

(51) Int. Cl.
*A61B 17/00* (2006.01)
*A61B 17/16* (2006.01)

(52) U.S. Cl.
CPC .................................. *A61B 17/1611* (2013.01)

(58) Field of Classification Search
CPC ........................ A61B 17/1604; A61B 17/1608
USPC ..................................................... 606/79, 83
See application file for complete search history.

(56) References Cited

U.S. PATENT DOCUMENTS

| | | | |
|---|---|---|---|
| 4,990,148 A | 2/1991 | Worrick, III et al. | |
| 5,273,519 A | 12/1993 | Koros et al. | |
| D460,553 S | 7/2002 | Koros et al. | |
| 6,520,979 B1 | 2/2003 | Loubens et al. | |
| 6,638,280 B2 | 10/2003 | Agbodoe | |
| 6,685,710 B2 | 2/2004 | Agbodoe et al. | |
| 6,699,254 B1 | 3/2004 | Tontarra | |
| 6,802,852 B2 | 10/2004 | Tontarra | |
| 6,991,633 B2 | 1/2006 | Agbodoe | |
| 7,377,933 B2 | 5/2008 | Martin | |
| 7,621,932 B2 * | 11/2009 | Wenzler | 606/184 |
| 7,691,107 B2 | 4/2010 | Schneiter | |
| 8,048,106 B2 * | 11/2011 | Widmann | 606/205 |
| 2007/0093843 A1 * | 4/2007 | Schneiter | 606/83 |

OTHER PUBLICATIONS

Clear Flush, Flushable Kerrison Rongeur, Jan. 2007, Boss Instruments.*
Clean-Cut Solutions, Rapidclean Detachable Kerrison Rongeurs, 2010, Codman & Shurtleff, Inc.*

* cited by examiner

*Primary Examiner* — Matthew Lawson
(74) *Attorney, Agent, or Firm* — Pandiscio & Pandiscio

(57) ABSTRACT

A rongeur comprising a bottom shaft comprising a proximal end, a distal end terminating in a footplate, a substantially flat upper surface extending along the bottom shaft, and a groove characterized by a wider proximal recess and a narrower distal recess comprising an undercut; a top shaft comprising a proximal end, a distal end, a substantially flat bottom surface extending along the top shaft, and a tongue characterized by a crossbar connected to the flat bottom surface by a vertical riser; wherein the flat bottom surface rests on the flat upper surface and the tongue is slidably disposed in the groove so that when the top shaft is moved distally relative to the bottom shaft, the tongue slides from the proximal recess into the distal recess; and further wherein the top shaft comprises a passageway for admitting air into the portion of the proximal recess vacated by the tongue.

14 Claims, 21 Drawing Sheets

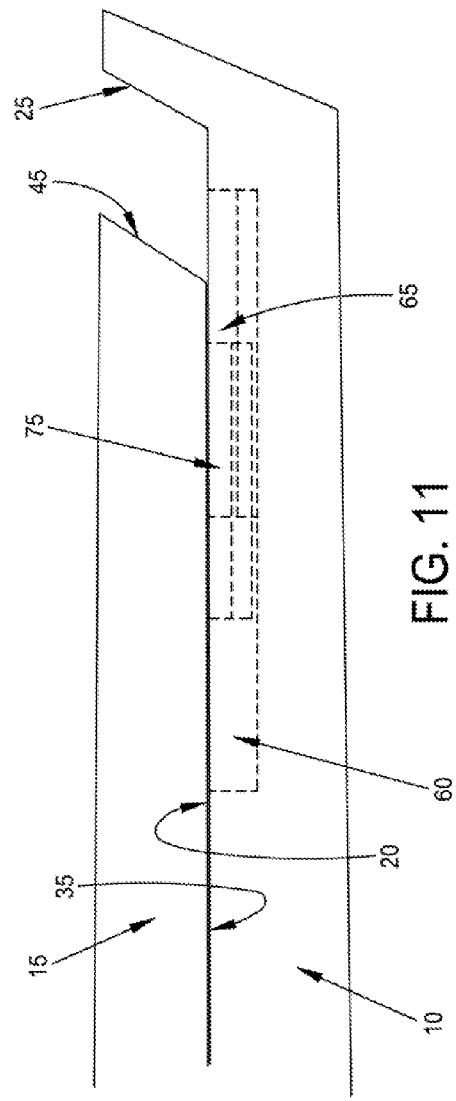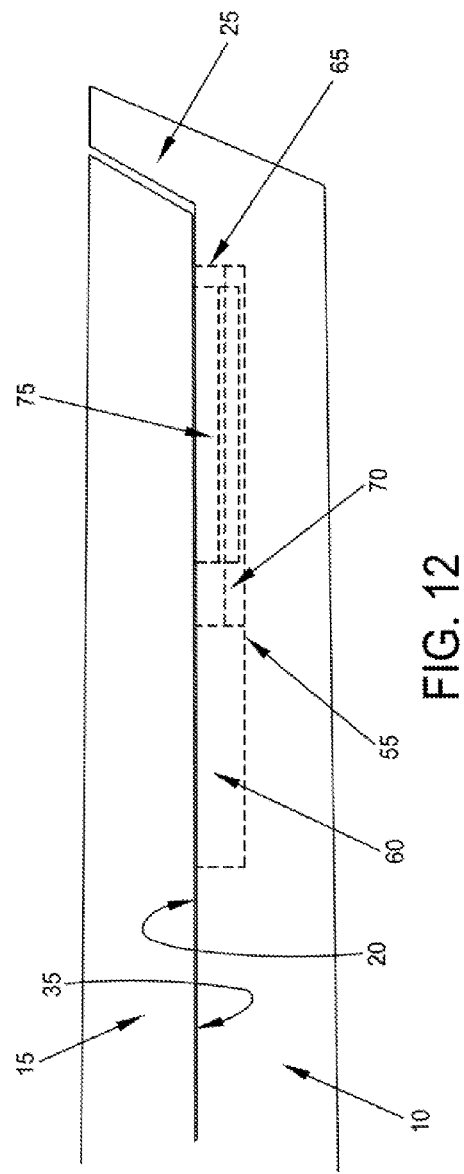

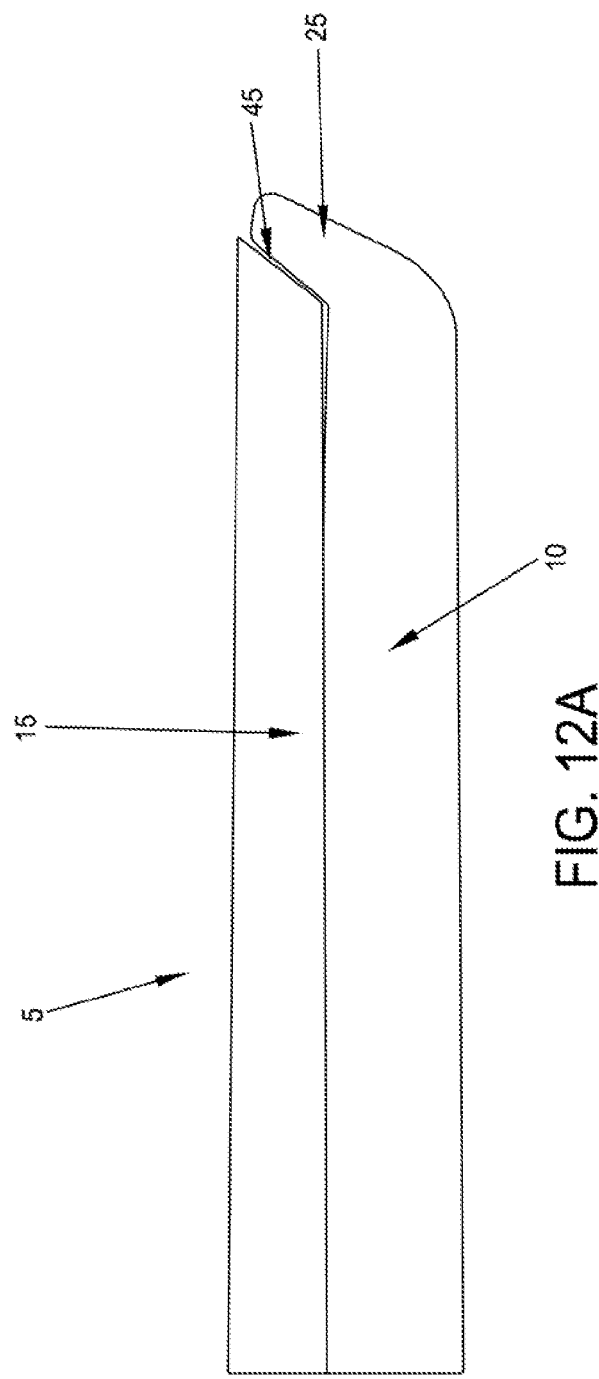

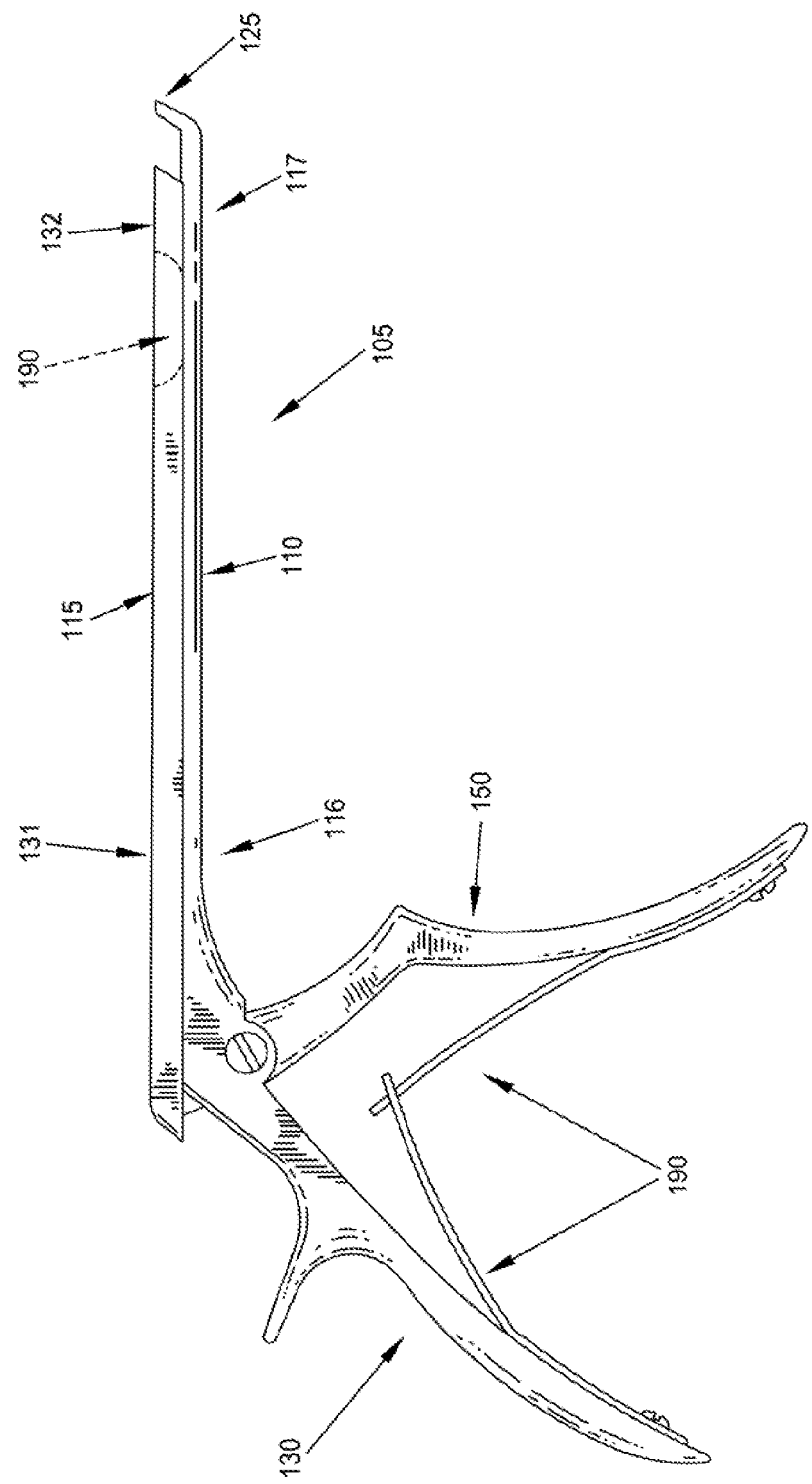

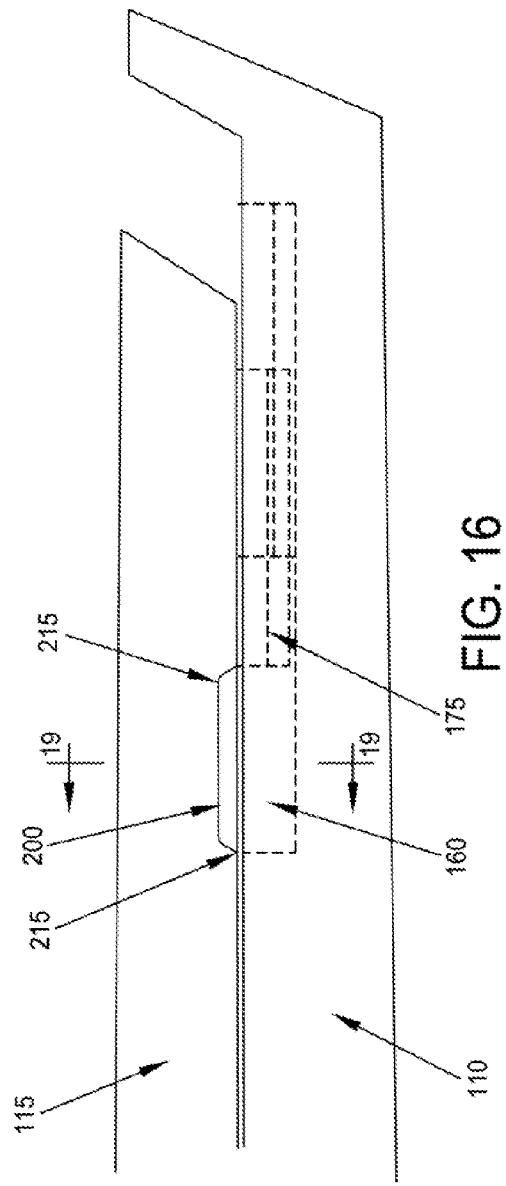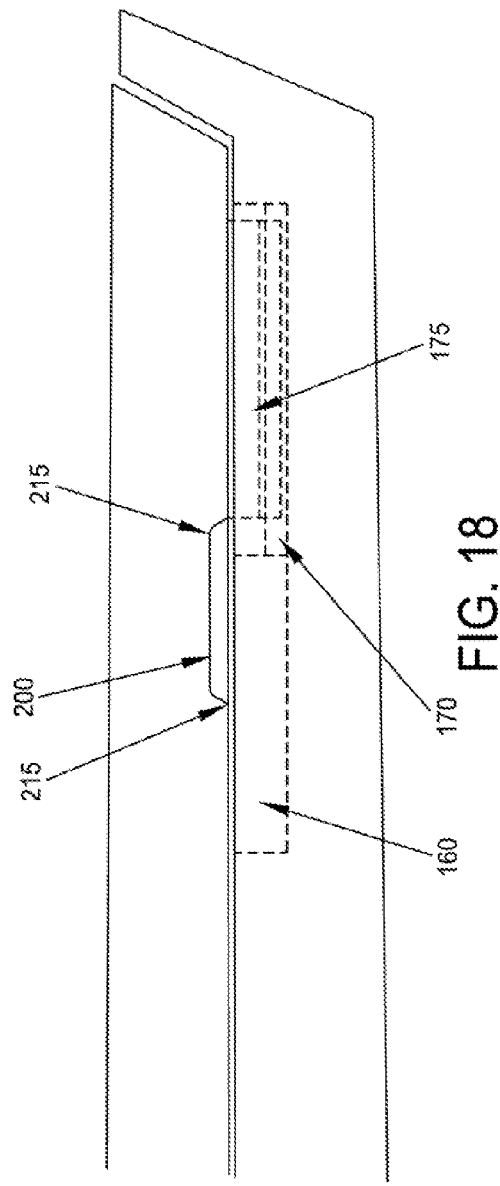

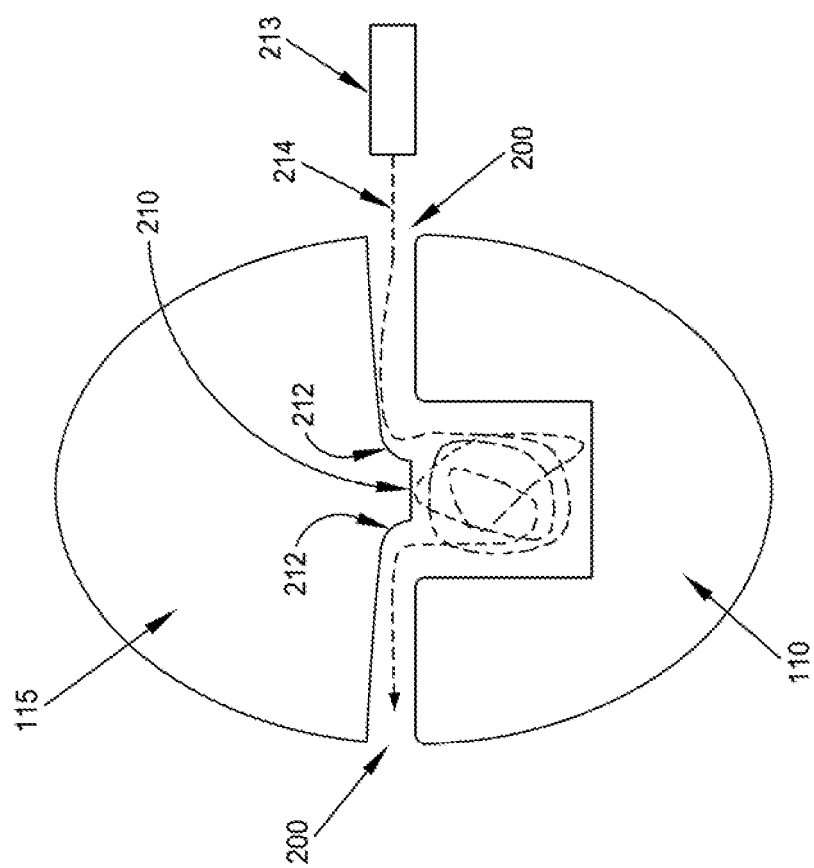

RONGEUR WITH VENTED T-SLIDE AND/OR INCREASED STRENGTH

REFERENCE TO PENDING PRIOR PATENT APPLICATIONS

This patent application claims benefit of:

(1) U.S. Provisional Patent Application Ser. No. 61/574,098, filed Jul. 28, 2011 by David Martin Funnell for RONGEUR WITH VENTED T-SLIDE AND METHOD FOR REMANUFACTURE;

(2) U.S. Provisional Patent Application Ser. No. 61/626,283, filed Sep. 26, 2011 by David Martin Funnell for RONGEUR WITH A VENTED T-SLOT AND METHOD FOR REMANUFACTURE; and (3) U.S. Provisional Patent Application Ser. No. 61/630,693, filed Dec. 19, 2011 by David Martin Funnel for STRENGTHENED RONGEUR WITH VENTED T-SLOT AND METHOD FOR REMANUFACTURE.

The three (3) above-identified patent applications are hereby incorporated herein by reference.

FIELD OF THE INVENTION

This invention relates to medical devices and apparatus in general, and more particularly to rongeurs for removing bone and other tissue.

BACKGROUND OF THE INVENTION

Rongeurs are medical devices that are typically used to remove bone and other tissue (e.g., cartilage) from a surgical site during a surgical procedure. Rongeurs of varying types and constructions are well known in the art.

Looking first at FIGS. 1-12, there is shown a typical prior art rongeur 5. Rongeur 5 comprises a bottom shaft 10 and a top shaft 15.

Bottom shaft 10 (FIGS. 1-5 and 9-12) generally comprises an elongated rigid shank having a proximal end 16 (FIG. 1) and a distal end 17 (FIG. 1). Bottom shaft 10 comprises a substantially flat upper surface 20 and terminates in a footplate 25 at the distal end of the shaft. Footplate 25 typically extends at a moderate obtuse angle with respect to the plane of upper surface 20. The proximal end of bottom shaft 10 typically terminates in a handle 30 (FIG. 1), which may be formed integral with bottom shaft 10 or may be otherwise connected thereto.

Top shaft 15 (FIGS. 1, 2, 6-12) generally comprises an elongated rigid shank having a proximal end 31 (FIG. 1) and a distal end 32 (FIG. 1). Top shaft 15 comprises a substantially flat bottom surface 35 and terminates in a concave surface 40 at the distal end of the shaft. Concave surface 40 is configured such that the edges of the distal end of the top shaft form a cutting edge 45 when top shaft 15 is applied against footplate 25 of bottom shaft 10. The proximal end of top shaft 15 is typically connected to a lever 50 (FIG. 1), which in turn is spring-biased away from handle 30, as will hereinafter be discussed in further detail.

Bottom shaft 10 further comprises a groove 55. Groove 55 is characterized by a wider proximal recess 60 and a narrower distal recess 65. Narrower distal recess 65 comprises an undercut 70.

Top shaft 15 further comprises a tongue 75 extending from bottom surface 35. Tongue 75 is characterized by a crossbar 80 which is connected to bottom surface 35 by a vertical riser 85. Tongue 75 of top shaft is sized to be slidably received in groove 55 of bottom shaft 10, whereby to form a T-slide connection.

Bottom shaft 10 and top shaft 15 are assembled together so that bottom surface 35 of top shaft 15 slides against top surface 20 of bottom shaft 10 and tongue 75 of top shaft 15 is slidably disposed in groove 55 of bottom shaft 10. This construction allows top shaft 15 to reciprocate longitudinally relative to bottom shaft 10 while remaining substantially parallel to, and in sliding engagement with, one another when top shaft 15 moves between (i) a resting position (i.e., where cutting edge 45 of top shaft 15 is spaced from footplate 25 of bottom shaft 10, as shown in FIGS. 1, 2 and 11), and (ii) a cutting position (i.e., where cutting edge 45 of top shaft 15 is in engagement with footplate 25 of bottom shaft 10, as shown in FIG. 12).

The reciprocating movement of top shaft 15 relative to bottom shaft 10 is typically effected by moving lever 50 (FIG. 1) proximally towards handle 30. More particularly, by virtue of the connection between top shaft 15 and lever 50, movement of lever 50 proximally causes top shaft 15 to slide distally relative to bottom shaft 10.

Preferably, springs 90 extend between handle 30 and lever 50 so that handle 30 and lever 50 remain separated from one another when rongeur 5 is in its resting (i.e., non-cutting) position (FIGS. 1, 2 and 11).

In use, the distal portion of rongeur 5 is deployed at a surgical site. Tissue targeted for removal is disposed between cutting edge 45 and footplate 25. Lever 50 is pulled proximally towards handle 30, which causes top shaft 15 to move distally along bottom shaft 10 until cutting edge 45 is brought into contact with footplate 25 (FIG. 12), thereby cutting the tissue disposed between cutting edge 45 and footplate 25. After cutting, lever 50 is released and top shaft 15 returns to its resting position (FIGS. 1, 2 and 11).

During use of rongeur 5, as top shaft 15 reciprocates relative to bottom shaft 10, top shaft 15 and bottom shaft 10 are kept in close vertical and horizontal alignment with each other as a result of the T-slide (i.e., tongue-and-groove) construction described above, with bottom surface 35 of top shaft 15 sliding along top surface 20 of bottom shaft 10. As top shaft 15 advances relative to bottom shaft 10, the distal movement of tongue 75 within groove 55 moves the proximal portion of tongue 75 from wider recess 60 into narrower recess 65. As this occurs, the volume of groove 55 which is disposed proximal to moving tongue 75 increases as tongue 75 moves distally. Inasmuch as bottom surface 35 of top shaft 15 makes a close sliding fit with top surface 20 of bottom shaft 10, this distal motion of tongue 75 creates a substantial suction force in the space proximal to the moving tongue, i.e., in wider recess 60. The result of this suction is that bone fragments, tissue debris and other bio-matter are drawn into wider recess 60, where they can collect and migrate to other portions of groove 55.

Unfortunately, it is difficult to remove bio-matter that collects in wider recess 60 without undertaking a time-consuming and uneconomical disassembly of rongeur 5. However, unless wider recess 60 and the rest of the rongeur can be effectively cleaned, the rongeur should not be used again because of the risk of contamination and spreading of pathogens. However, one-time use of an expensive piece of surgical equipment is undesirable at best, and effectively impractical with rongeurs.

As a result, one object of the present invention is to provide a novel rongeur that eliminates the suction force resulting from the movement of tongue 75 into narrower recess 65 so as to prevent the collection of bio-matter and other debris in wider recess 60 of bottom shaft 10 of rongeur 5.

An additional problem associated with prior art rongeurs is that the formation of groove 55 in general, and the formation of undercut 70 along narrower recess 65 in particular, tends to weaken the distal portion of bottom shaft 10 because it requires the removal of a substantial amount of the material that makes up the distal portion of bottom shaft 10 (e.g., metal). This is a particular problem as users of rongeurs frequently apply a substantial amount of force when actuating the device in order to cut tough tissue, which can cause the distal portion of bottom shaft 10 to bend during use, as inclined cutting edge 45 exerts a significant force against inclined footplate 25. See FIG. 12A. Such bending can substantially impair the efficiency and effectiveness of prior art rongeurs.

Accordingly, another object of the present invention is to provide for a strengthened rongeur.

SUMMARY OF THE INVENTION

These and other objects of the present invention are addressed by the provision and use of a novel rongeur that (i) eliminates the suction force resulting from the advancement of a top shaft relative to a bottom shaft in order to prevent the collection of bio-matter and other debris in a groove formed in the bottom shaft; and (ii) provides for a strengthened rongeur by altering the shape of the tongue in the top shaft and the groove in the bottom shaft so that less of the material in the bottom shaft needs to be removed from the bottom shaft in order to form the groove.

In one preferred form of the present invention, there is provided a rongeur comprising:

a bottom shaft comprising a proximal end and a distal end and a substantially flat upper surface extending along at least a portion of the bottom shaft, the distal end terminating in a footplate;

a top shaft comprising a proximal end and a distal end and a substantially flat bottom surface extending along at least a portion of the top shaft;

wherein the bottom shaft comprises a groove characterized by a wider proximal recess and a narrower distal recess, the distal recess comprising an undercut;

wherein the top shaft comprises a tongue characterized by a crossbar connected to the bottom surface of the top shaft by a vertical riser;

wherein at least a portion of the flat bottom surface of the top shaft rests on at least a portion of the flat upper surface of the bottom shaft and the tongue is slidably disposed in the groove so that when the top shaft is moved distally relative to the bottom shaft, the tongue slides from the wider proximal recess into the narrower distal recess;

and further wherein the top shaft comprises at least one passageway for admitting air into the portion of the wider proximal recess vacated by the tongue.

In another preferred form of the present invention, there is provided a rongeur comprising:

a bottom shaft comprising a proximal end and a distal end, and an upper surface having a groove formed therein, the distal end terminating in a footplate;

a top shaft comprising a proximal end and a distal end, and a bottom surface having a tongue projecting downwardly therefrom;

the bottom surface of the top shaft being slidably disposed on the upper surface of the bottom shaft, and the tongue being slidably disposed in the groove, so that when the top shaft is moved distally relative to the bottom shaft, the tongue slides distally within the groove;

and further wherein the top shaft comprises at least one passageway for admitting air into the portion of the groove vacated by the tongue, whereby to eliminate the potential to generate suction force in the portion of the groove vacated by the tongue as the top shaft moves distally.

In another preferred form of the present invention, there is provided a rongeur comprising:

a bottom shaft comprising a proximal end and a distal end and a substantially flat upper surface extending along at least a portion of the bottom shaft, the distal end terminating in a footplate;

a top shaft comprising a proximal end and a distal end and a substantially flat bottom surface extending along at least a portion of the top shaft;

wherein the bottom shaft comprises a groove characterized by a wider proximal recess and a narrower distal recess, the distal recess comprising an undercut;

wherein the top shaft comprises a tongue characterized by a crossbar connected to the bottom surface of the top shaft by a vertical riser;

wherein at least a portion of the flat bottom surface of the top shaft rests on at least a portion of the flat upper surface of the bottom shaft and the tongue is slidably disposed in the groove so that when the top shaft is moved distally relative to the bottom shaft, the tongue slides from the wider proximal recess into the narrower distal recess;

and further wherein the floor of the undercut is formed with rounded edges and the bottom of the crossbar is formed with rounded edges.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 11 is a side view of the top shaft and bottom shaft of the prior art rongeur of FIG. 1, with the top shaft in its resting (or open) position;

FIG. 12 is a side view of the top shaft and bottom shaft of the prior art rongeur of FIG. 1, with the top shaft in its cutting position;

FIG. 12A is a schematic view showing how the bottom shaft of the rongeur can become bent during heavy use;

FIG. 13 is a schematic view of a novel rongeur formed in accordance with the present invention;

FIG. 16 is a side view of the distal portion of another novel rongeur formed in accordance with the present invention, with the top shaft in its resting (or open) position;

FIG. 18 is a side view of the novel rongeur of FIG. 16, with the top shaft in its cutting position;

FIG. 19A is a schematic view showing how arcuate surfaces formed on the top shaft of the rongeur can direct a jet of cleaning fluid into the groove formed in the bottom shaft.

DETAILED DESCRIPTION OF THE PREFERRED EMBODIMENTS

Figure 1:
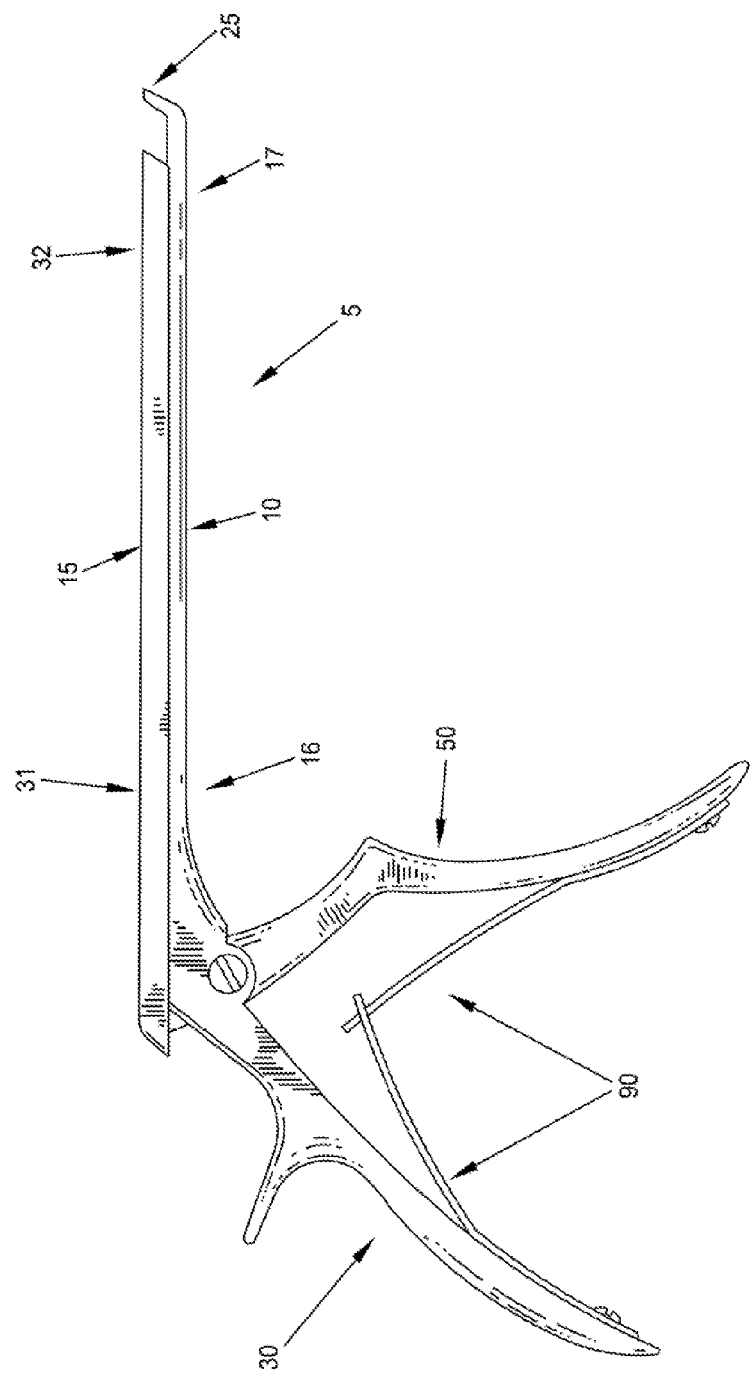
FIG. 1 is a schematic view of a prior art rongeur.
Figure 2:
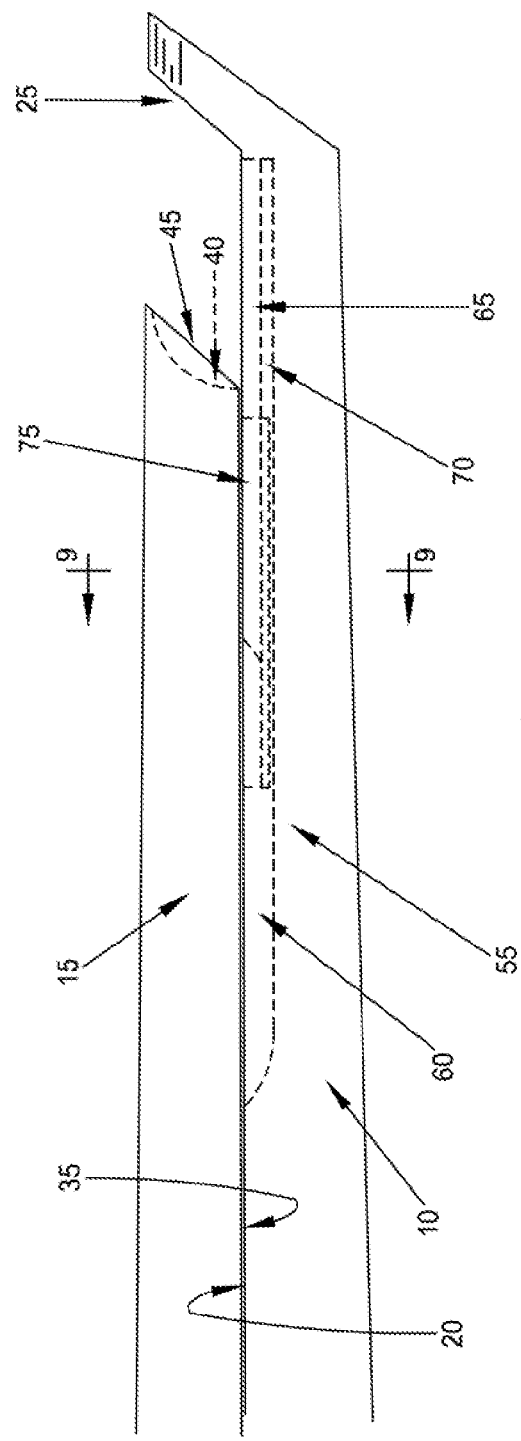
FIG. 2 is a side view of the distal portion of the prior art rongeur of FIG. 1, with the top shaft in its resting (or open) position.
Figure 3:
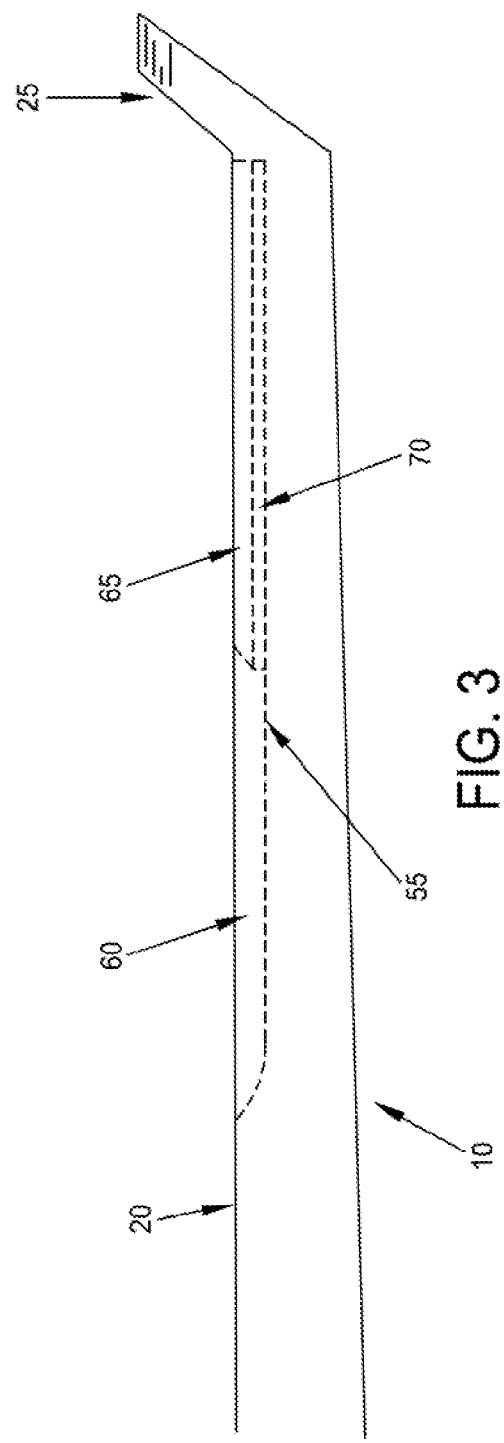
FIG. 3 is side view of the bottom shaft of the prior art rongeur of FIG. 1.
Figure 4:
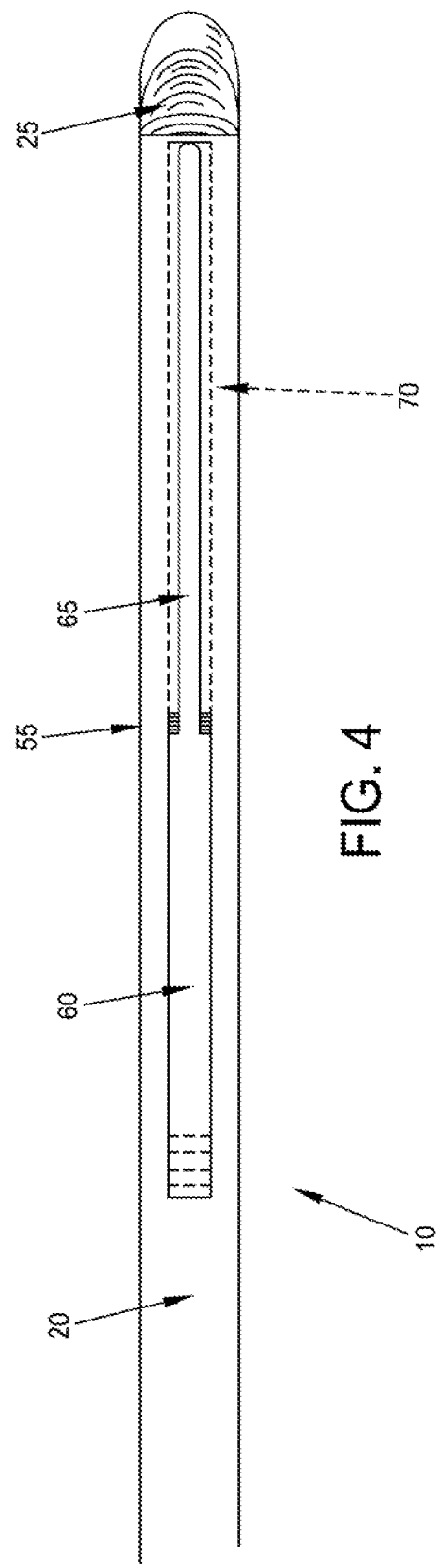
FIG. 4 is a top view of the bottom shaft of the prior art rongeur of FIG. 1.
Figure 5:
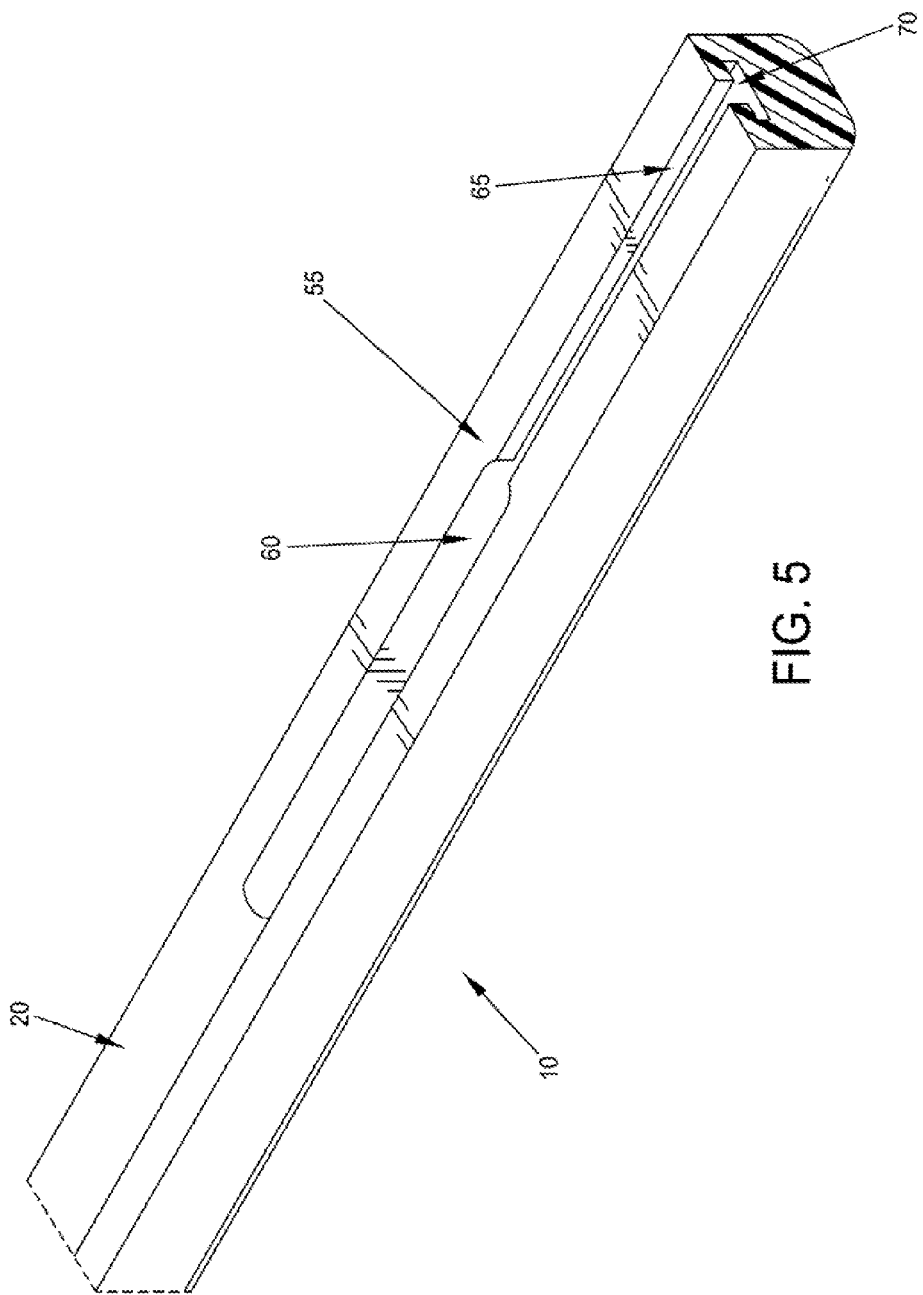
FIG. 5 is a perspective view of a portion of the bottom shaft of the prior art rongeur of FIG. 1.
Figure 6:
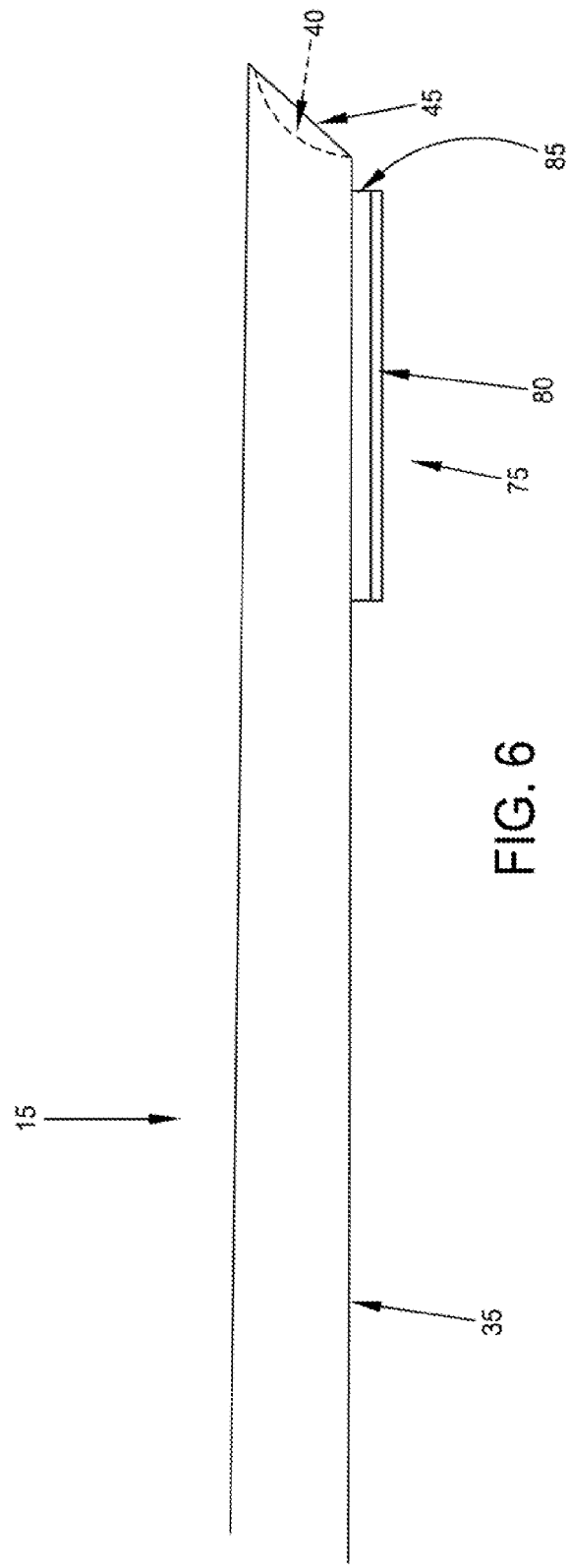
FIG. 6 is a side view of the top shaft of the prior art rongeur of FIG. 1.
Figure 7:
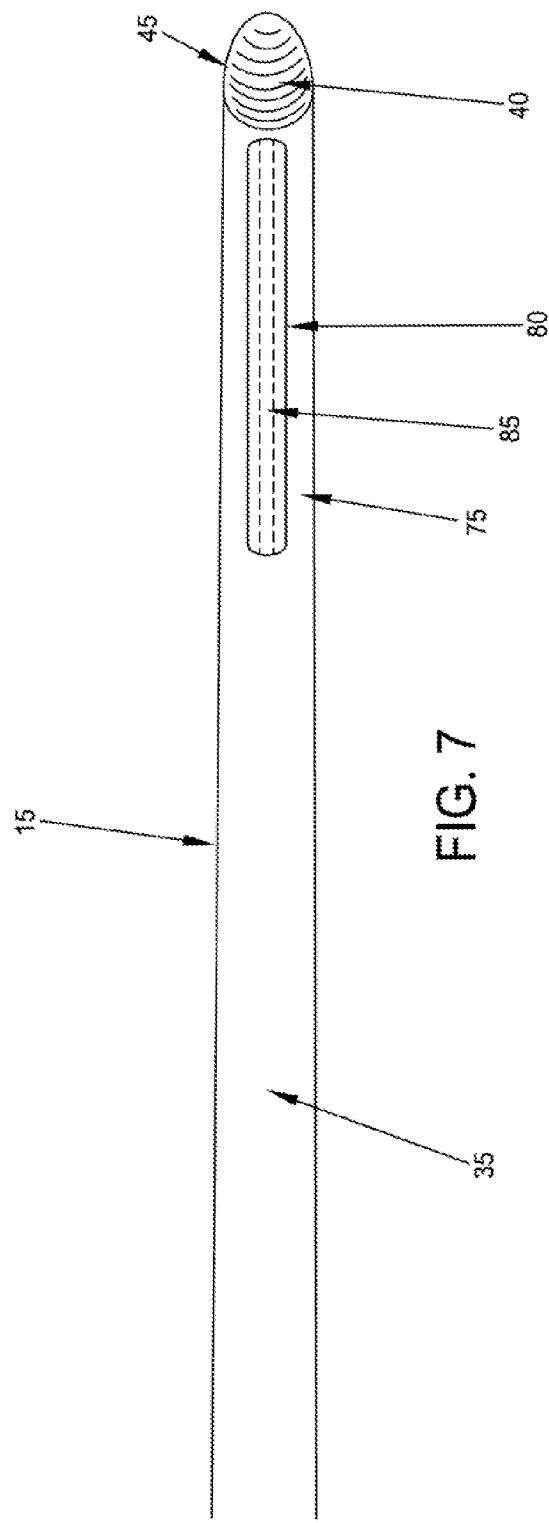
FIG. 7 is a bottom view of the top shaft of the prior art rongeur of FIG. 1.
Figure 8:
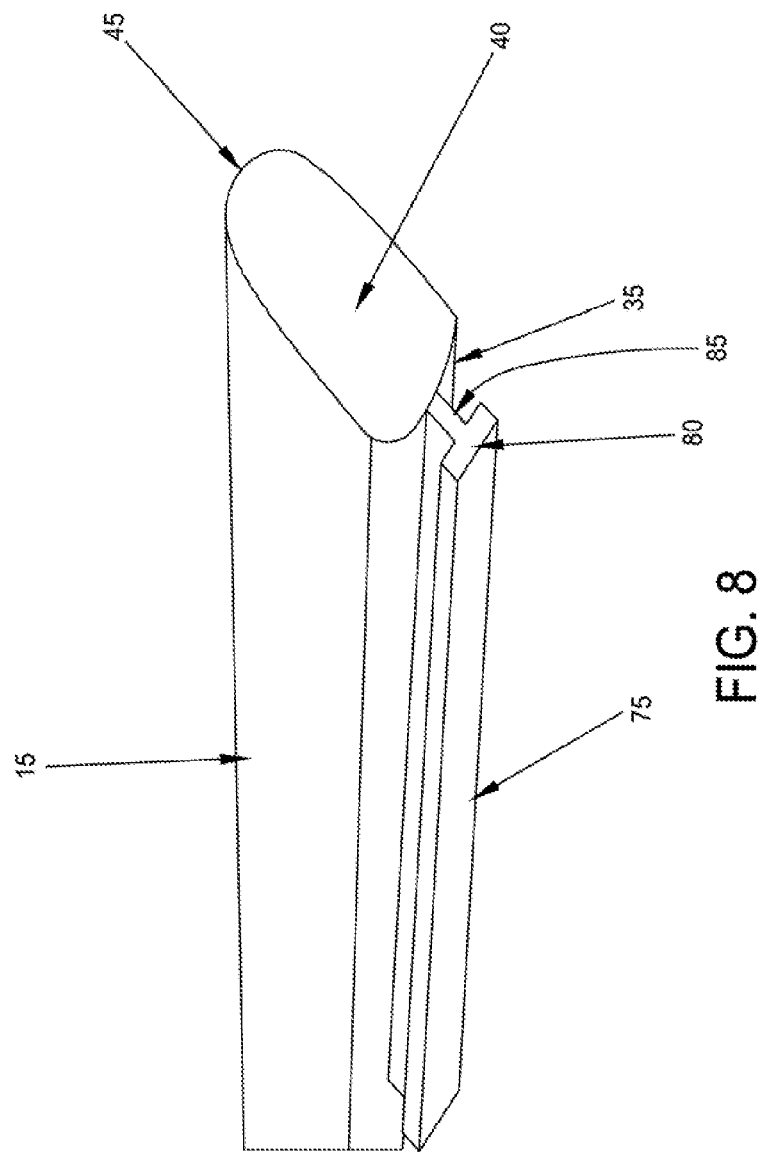
FIG. 8 is a perspective view of a portion of the top shaft of the prior art rongeur of FIG. 1.
Figure 9:
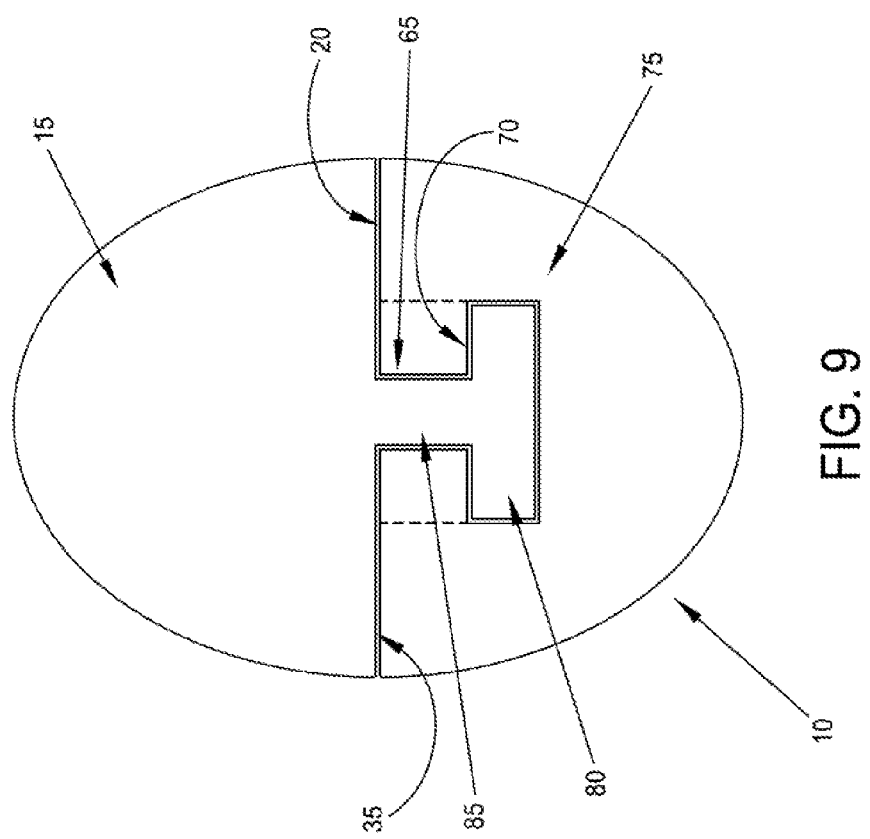
FIG. 9 is a cross-sectional view taken along line 9-9 of FIG. 2.
Figure 10:
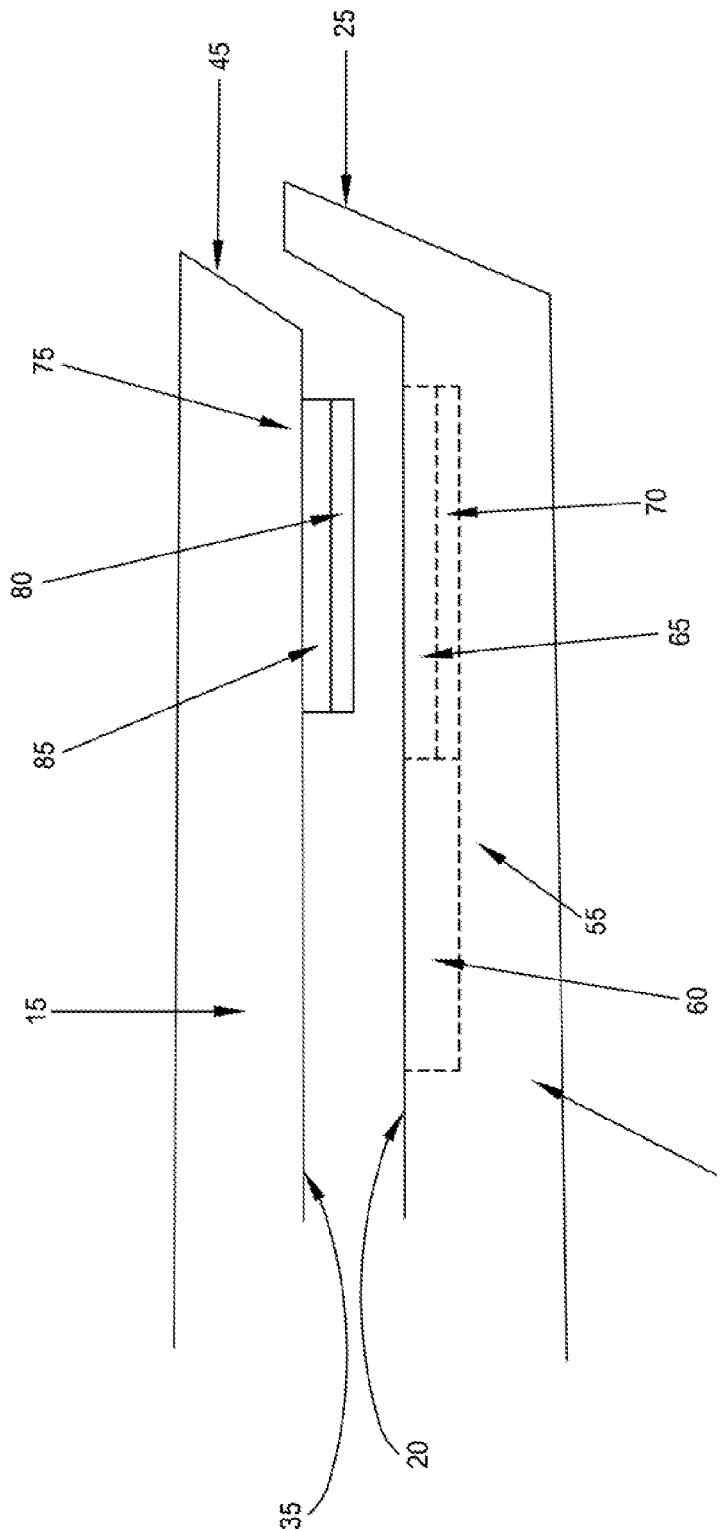
FIG. 10 is an exploded side view of the top shaft and bottom shaft of the prior art rongeur of FIG. 1.

Looking now at FIGS. 13, 13A, 14 and 15, there is shown a novel rongeur 105 formed in accordance with the present invention. Rongeur 105 comprises a bottom shaft 110 and a top shaft 115.

Bottom shaft 110 generally comprises an elongated rigid shank having a proximal end 116 (FIG. 13) and a distal end 117 (FIG. 13). Bottom shaft 110 comprises a substantially flat upper surface 120 and terminates in a footplate 125 at the distal end of the shaft. Footplate 125 extends at a moderate obtuse angle with respect to the plane of upper surface 120. The proximal end of bottom shaft 110 terminates in a handle 130 (FIG. 13), which may be formed integral with bottom shaft 110 or may be otherwise connected thereto.

Top shaft 115 generally comprises an elongated rigid shank having a proximal end 131 (FIG. 13) and a distal end 132 (FIG. 13). Top shaft 115 comprises a substantially flat bottom surface 135 and terminates in a concave surface 140 at the distal end of the shaft. Concave surface 140 is configured such that the edges of the distal end of the top shaft form a cutting edge 145 when top shaft 115 is applied against footplate 125 of bottom shaft 110. The proximal end of top shaft 115 is connected to a lever 150 (FIG. 13), which in turn is spring-biased away from handle 130, as will hereinafter be discussed in further detail.

Bottom shaft 110 further comprises a groove 155. Groove 155 is characterized by a wider proximal recess 160 and a narrower distal recess 165. Narrower distal recess 165 comprises an undercut 170.

Top shaft 115 further comprises a tongue 175 extending from bottom surface 135. Tongue 175 is characterized by a crossbar 180 which is connected to bottom surface 135 by a vertical riser 185. Tongue 175 of the top shaft is sized to be slidably received in groove 155 of bottom shaft 110, whereby to form a T-slide connection.

Figure 13A:
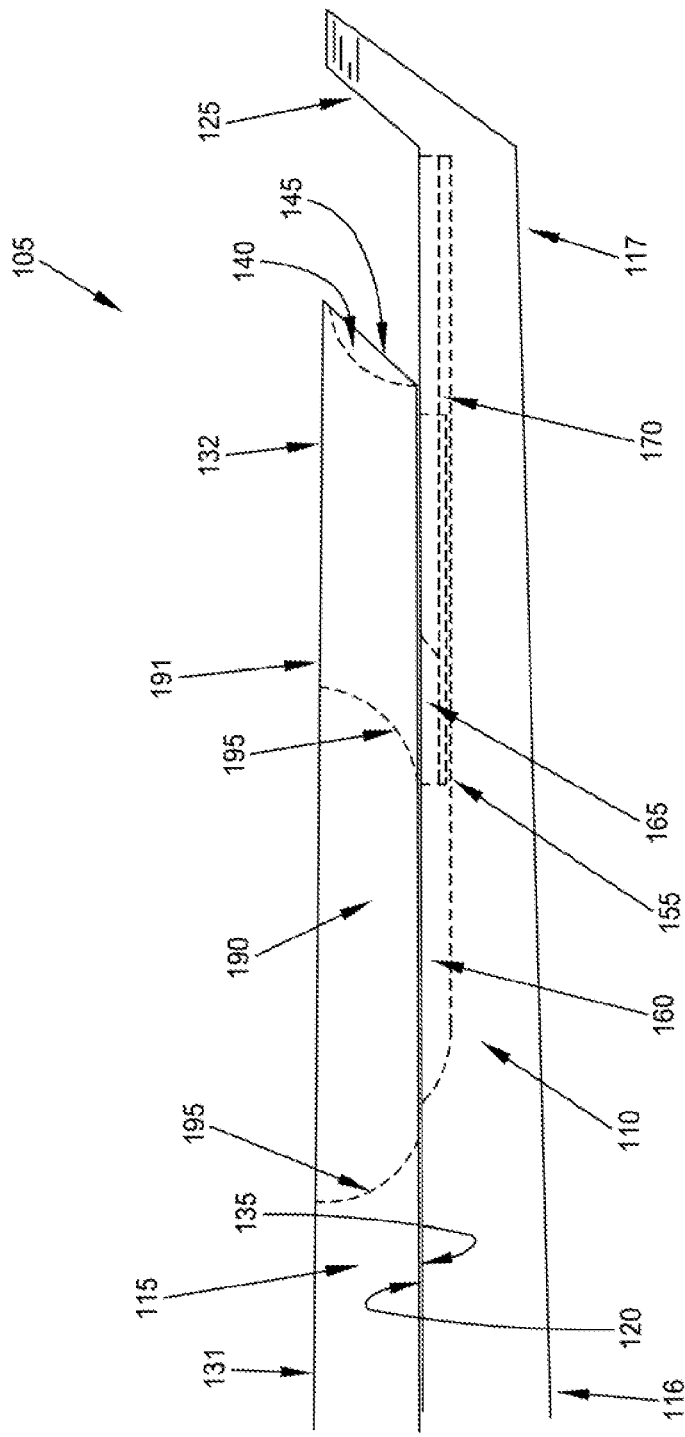
FIG. 13A is a side view of the distal portion of the novel rongeur of FIG. 13, with the top shaft in its resting (or open) position.
Figure 13B:
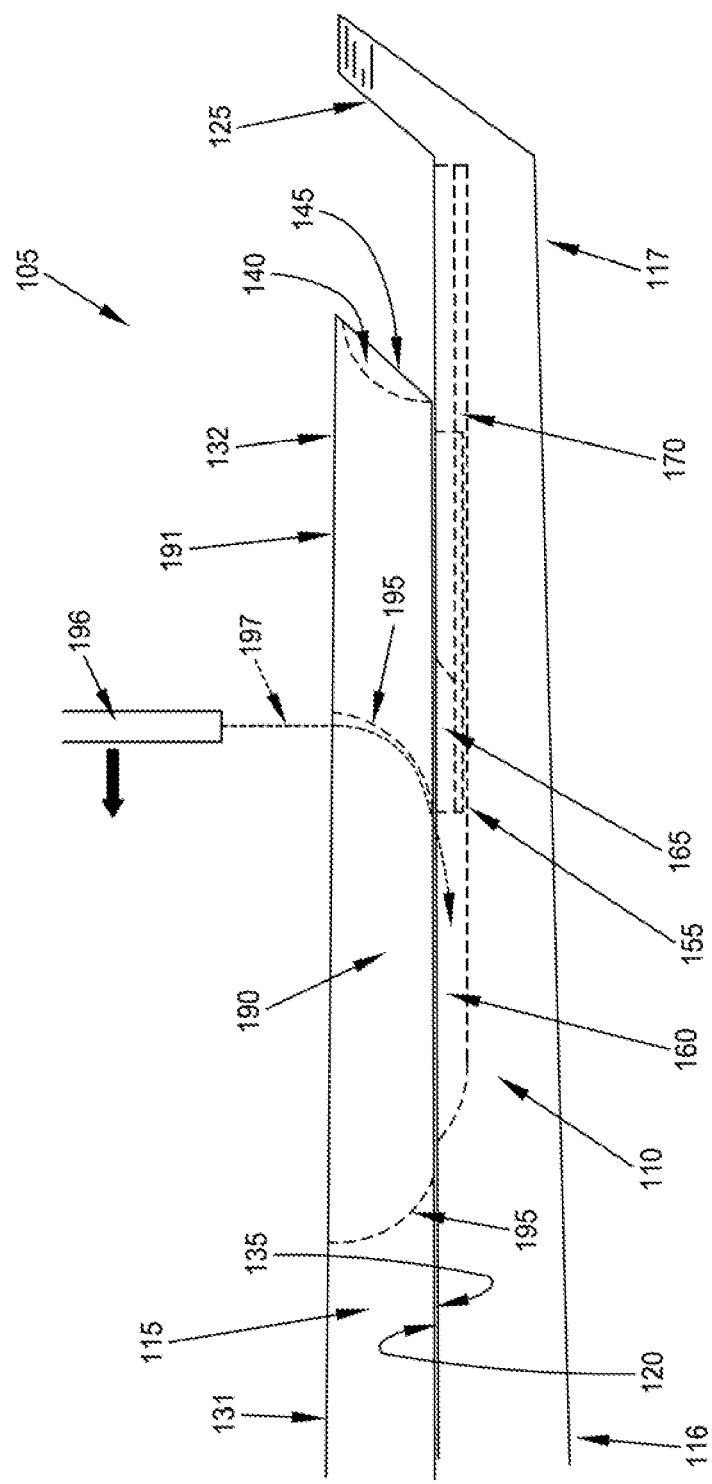
FIG. 13B is a schematic view showing how arcuate surfaces formed on the top shaft of the rongeur can direct a jet of cleaning fluid into the groove formed in the bottom shaft.
Figure 14:
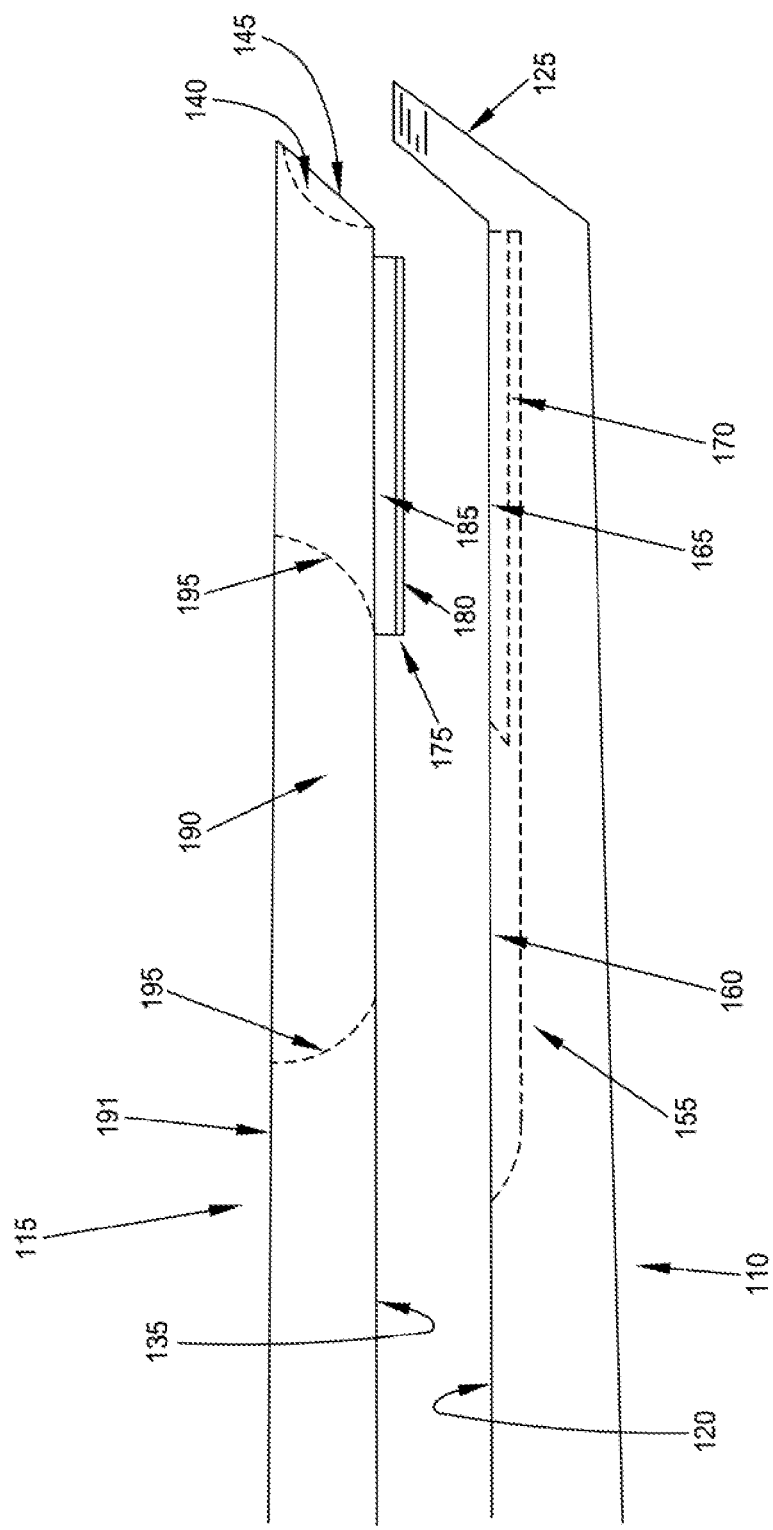
FIG. 14 is an exploded side view of the top shaft and bottom shaft of the novel rongeur shown in FIGS. 13 and 13A.
Figure 15:
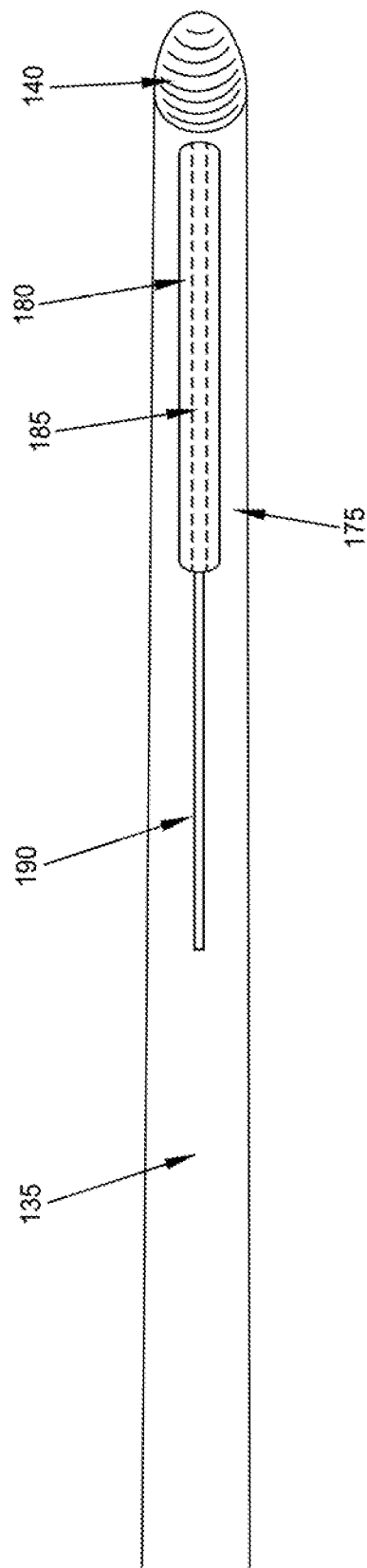
FIG. 15 is a bottom view of the top shaft of the novel rongeur shown in FIGS. 13 and 13A.
Figure 17:
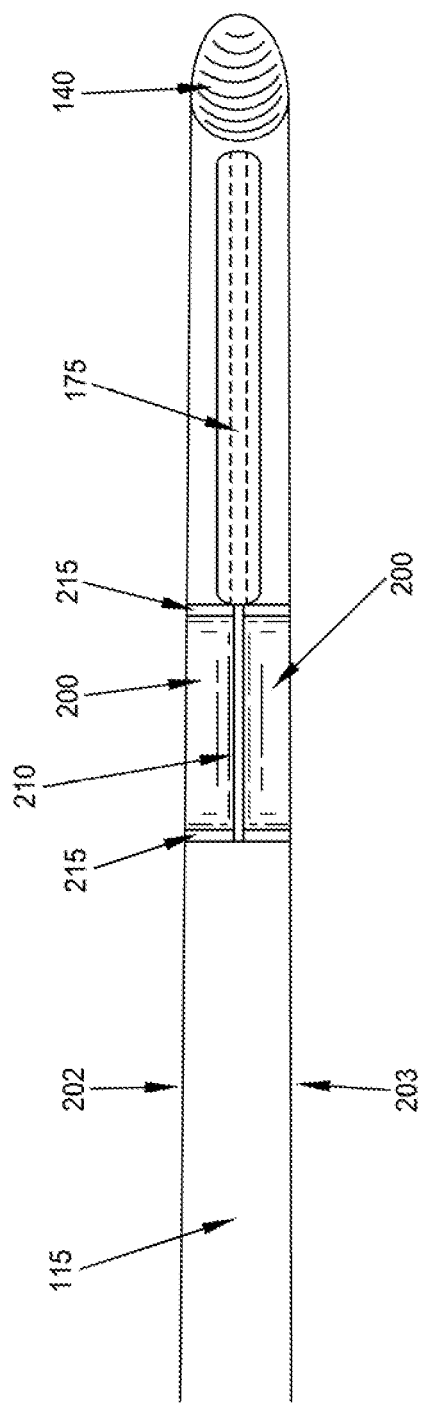
FIG. 17 is a bottom view of the top shaft of the novel rongeur of FIG. 16.

Bottom shaft 110 and top shaft 115 are assembled together so that bottom surface 135 of top shaft 115 slides against top surface 120 of bottom shaft 110 and tongue 175 of top shaft 115 is slidably disposed in groove 155 of bottom shaft 110. This construction allows top shaft 115 to reciprocate longitudinally relative to bottom shaft 110 while remaining substantially parallel to, and in sliding engagement with, one another when top shaft 115 moves between (i) a resting position (i.e., where cutting edge 145 of top shaft 115 is spaced from footplate 125 of bottom shaft 110, as shown in FIGS. 13 and 13A), and (ii) a cutting position (i.e., where cutting edge 145 of top shaft 115 is in engagement with footplate 125 of bottom shaft 110).

In accordance with the present invention, top shaft 115 further comprises at least one passageway for allowing air to pass through top shaft and into wider proximal recess 160 of groove 155, whereby to eliminate the potential to generate a suction force in wider proximal recess 160 of groove 155 when top shaft 115 advances relative to bottom shaft 110.

More particularly, in one form of the present invention, a passageway 190 is formed vertically through top shaft 115, opening on the top surface 191 of top shaft 115 and on the bottom surface 135 of top shaft 115. Passageway 190 is preferably in the form of an elongated slit extending longitudinally from the proximal end of tongue 175 to a point on top shaft 115 approximately adjacent to the proximal end of wider recess 160 when top shaft 115 of rongeur 105 is in its resting (or open) position. See FIG. 13A. Passageway 190 allows air to pass into wider proximal recess 160 of groove 155 of bottom shaft 110, whereby to eliminate the potential to create suction by the distal movement of tongue 175 into narrower recess 165 of groove 155, whereby to prevent the collection of bio-matter and other debris in groove 155 of the bottom shaft of the rongeur.

The dimension and relative position of passageway 190 on the top shaft 115 is a significant aspect of the present invention. More particularly, passageway 190 must be sufficiently long, and appropriately positioned, so as to ensure that at least a portion of passageway 190 is always in fluid communication with wider recess 160 of groove 155 regardless of the longitudinal position of top shaft 115 vis-à-vis bottom shaft 110.

Further, it has been discovered that, by forming top shaft 115 with the aforementioned passageway 190, cleaning and sterilization of rongeur 105 is significantly facilitated, since passageway 190 allows jets of cleaning fluid to reach the portions of groove 155 proximal to tongue 175 during cleaning, and since passageway 190 allows high temperature steam to reach the portions of groove 155 proximal to tongue 175 during autoclaving. This makes it possible to clean and sterilize rongeur 105 without requiring disassembly. Significantly, by forming passageway 190 with upwardly rounded proximal and distal ends 195 (see FIGS. 13A and 14), the jets of cleaning fluid and/or high temperature steam are better able to pass through passageway 190 to clean and/or sterilize the portions of groove 155 proximal to tongue 175. See, for example, FIG. 13B, which shows a cleaning tool 196 directing a jet 197 of cleaning fluid into passageway 190, with jet 197 being directed into wider recess 160 of groove 155 by one of the arcuate surfaces 195.

In another form of the present invention, and looking now at FIGS. 16-19, at least one passageway 200 is formed in the side wall of top shaft 115 so as to allow air to pass by top shaft 115 and into wider proximal recess 160 of groove 155. The at least one passageway 200 extends, longitudinally, from the proximal end of tongue 175 to a point on top shaft 115 approximately adjacent to the proximal end of wider recess 160 when top shaft 115 of rongeur 105 is in its resting (or open) position (FIG. 16). The at least one passageway 200 may be formed in top shaft 115 by removing material from a portion of a side of top shaft 115 (e.g., through grinding, cutting or other ways well known in the art of machining parts). The at least one passageway 200 serves to admit air into wider proximal recess 160 of groove 155 of bottom shaft 110, whereby to eliminate the potential to create suction by the distal movement of tongue 175 into narrower recess 165 of groove 155, whereby to prevent the collection of biomatter and other debris in groove 155 of the bottom shaft of the rongeur.

In one preferred form of the invention, two passageways 200 are formed in top shaft 115, one opening on each side surface 202, 203 (FIG. 17) of top shaft 115, so as to form two aligned openings 200, with a portion 210 (FIGS. 17 and 19) of bottom surface 135 remaining between the two openings 200. Leaving portion 210 of bottom surface 135 helps stabilize top shaft 115 as it reciprocates along top surface 120 of bottom shaft 110 during use of rongeur 105.

The dimension and relative position of passageways 200 on the top shaft 115 is a significant aspect of the present invention. More particularly, passageways 200 must be sufficiently long, and appropriately positioned, so as to ensure that at least a portion of passageways 200 are always in fluid communication with wider recess 160 of groove 155 regardless of the longitudinal position of top shaft 115 vis-à-vis bottom shaft 110.

In addition to the foregoing, passageways 200 (FIGS. 16-19) formed in top shaft 115 facilitate cleaning and sterilization of rongeur 105, since passageways 200 allow jets of cleaning fluid to reach the portions of groove 155 proximal to tongue 175 during cleaning, and since passageways 200 allow high temperature steam to reach the portions of groove 155 proximal to tongue 175 during autoclaving. This makes it possible to clean and sterilize rongeur 105 without requiring disassembly. Significantly, by forming portion 210 with arcuate edges 212 (FIG. 19), the jets of cleaning fluid and/or high temperature steam are better able to pass through passageways 200 to clean and/or sterilize the portions of groove 155 proximal to tongue 175. See, for example, FIG. 19A, which shows a cleaning tool 213 directing a jet 214 of cleaning fluid into passageway 200, with jet 214 being directed into wider recess 160 of groove 155 by one of the arcuate surfaces 212.

If desired, the aforementioned passageways 190 and 200 may be provided on the same rongeur.

Significantly, the aforementioned passageway 190 and/or passageway 200 may be provided at the time of manufacture of the rongeur or, alternatively, they may be provided retroactively to existing rongeurs.

In yet another form of the present invention, a rongeur having a strengthened bottom shaft is provided. The bottom shaft of the rongeur is strengthened by altering the configuration of the groove formed in the bottom shaft of the rongeur, (and, correspondingly, by altering the configuration of the tongue formed on the top shaft of the rongeur) so that less of the material in the bottom shaft needs to be removed from the bottom shaft in order to form the groove 155. Thus, altering the configuration of the groove 155 in the bottom shaft 115 provides for a bottom shaft that better resists bending in response to the forces exerted by the top shaft 115 on footplate 125 during use of the rongeur.

Figure 20:
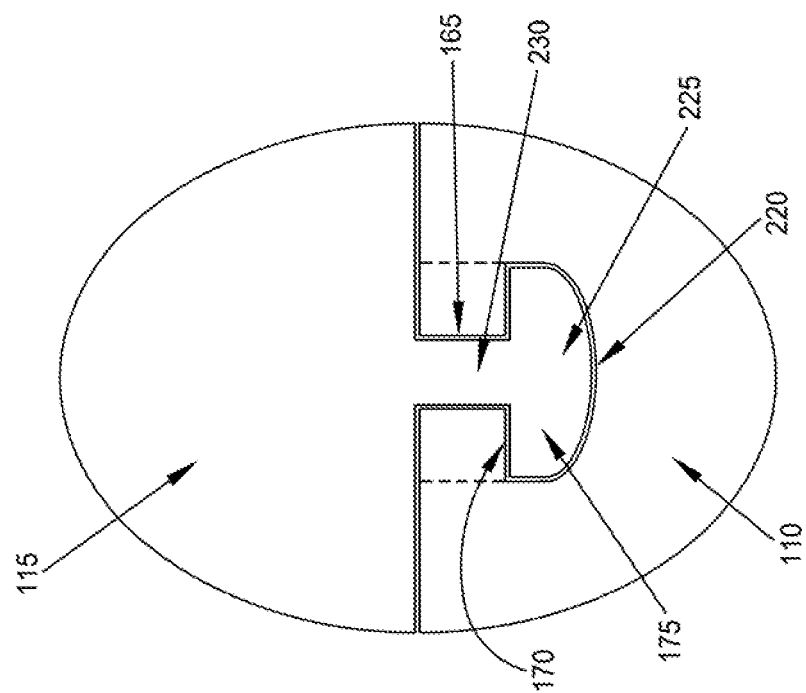
FIG. 20 is a cross-sectional view of the top shaft and bottom shaft of another novel rongeur formed in accordance with the present invention.
Figure 19:
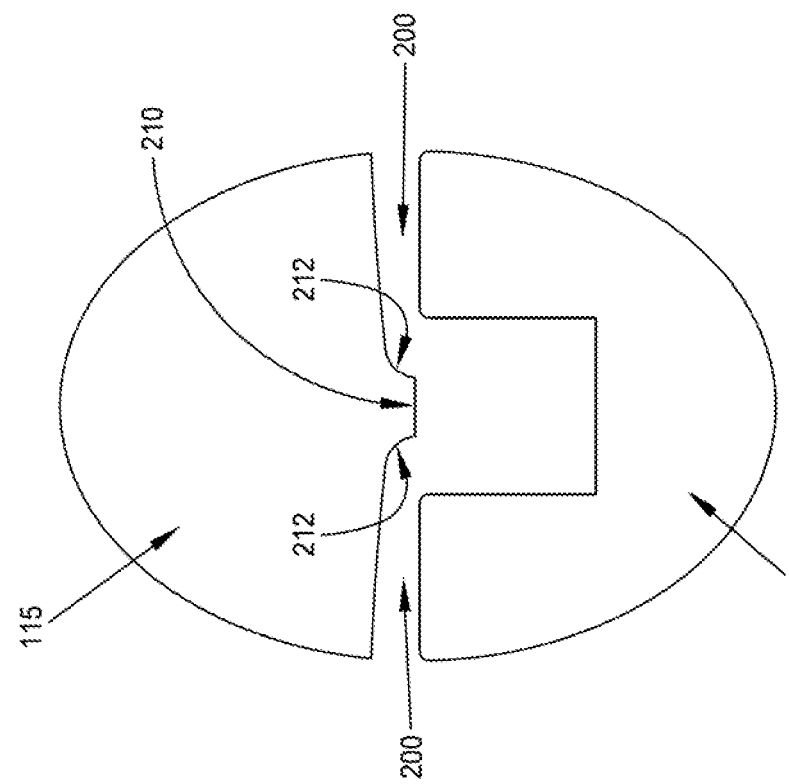
FIG. 19 is a cross-sectional view taken along line 19-19 of FIG. 16.

More particularly, and looking now at FIG. 20, in this form of the invention, bottom shaft 110 comprises a groove 220 which is generally similar to the groove 155 discussed above, except that at least the undercut 170 of groove 220 (and, if desired, the entire length of groove 220) is formed with a rounded floor (i.e., a rounded bottom surface) instead of a flat floor (i.e., a flat bottom surface). Correspondingly, top shaft 115 comprises a tongue 175 which comprises a crossbar 225 which is formed with a rounded bottom surface which is the inverse of the rounded floor of undercut 170.

In essence, the shape of undercut 170 of bottom shaft 110 and crossbar 225 of top shaft 115 are formed in complementary shapes that roughly resemble the shape of an inverted mushroom. Forming undercut 170 and crossbar 225 in this manner requires that less material be removed from bottom shaft 110 during formation of groove 220 than where groove 220 and crossbar 225 are formed with flat bottoms. The retention of a larger amount of rigid material in bottom shaft 110 provides enhanced resistance against the undesirable bending of bottom shaft 110 when a significant force is applied by the user of the rongeur to top shaft 115 against footplate 125 during use of the rongeur. Further, the concave shape of the floor of undercut 170 distributes stresses in a superior manner to a flat floor, thereby providing additional strength and rigidity to bottom shaft 110.

Preferably, the interior angles of undercut 170 and crossbar 180 are square and not filleted or otherwise rounded (i.e., the ceiling of undercut 170, and the upper surface of crossbar 180, are flat). It has been discovered that filleted interior angles can lead to an undesirably loose or less robust engagement of tongue 175 of the top shaft 115 within groove 220 of bottom shaft 110. A tight, slidable engagement between tongue 175 and groove 220 is important to the proper functioning of the rongeur during use, as "play" between top shaft 115 and bottom shaft 110 can degrade performance of the rongeur by dispersing forces intended to cut tissue or bone positioned between cutting edge 145 of top shaft 115 and footplate 125 of bottom shaft 110, could cause the rongeur to operate outside of tolerances, could cause the T-slide connection to bind during use or, in an extreme case, could lead to disengagement of bottom shaft 110 and top shaft 115 during use of the rongeur.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A rongeur comprising:
a bottom shaft comprising a proximal end and a distal end and a substantially flat upper surface extending along at least a portion of the bottom shaft, the distal end terminating in a footplate;
a top shaft comprising a proximal end and a distal end, at least one side surface disposed between the proximal end and the distal end, and a substantially flat bottom surface extending along at least a portion of the top shaft;
wherein the bottom shaft comprises a groove characterized by a wider proximal recess and a narrower distal recess, the distal recess comprising an undercut;
wherein the top shaft comprises a tongue characterized by a crossbar connected to the bottom surface of the top shaft by a vertical riser;
wherein at least a portion of the flat bottom surface of the top shaft rests on at least a portion of the flat upper surface of the bottom shaft and the tongue is slidably disposed in the groove so that when the top shaft is moved distally relative to the bottom shaft, the tongue slides from the wider proximal recess into the narrower distal recess;

and at least one laterally-extending passageway formed within the top shaft for admitting air into the portion of the wider proximal recess vacated by the tongue, wherein the at least one passageway opens on the at least one side surface and the bottom surface of the top shaft and is in fluid communication with the groove, wherein the at least one passageway is laterally aligned with at least a portion of the wider proximal recess of the groove in the bottom shaft regardless of the disposition of the top shaft relative to the bottom shaft.

2. A rongeur according to claim 1 wherein the at least one laterally-extending passageway is formed in the at least one side surface of the top shaft.

3. A rongeur according to claim 2 wherein the at least one laterally-extending passageway extends across only a portion of the full width of the top shaft.

4. A rongeur according to claim 3 wherein the at least laterally-extending one passageway comprises a second laterally-extending passageway formed in the at least one side surface of the top shaft.

5. A rongeur according to claim 4 wherein the two laterally-extending passageways are offset from one another.

6. A rongeur according to claim 5 wherein the two laterally-extending passageways are separated by a midline ridge.

7. A rongeur according to claim 6 wherein the midline ridge comprises arcuate surfaces.

8. A rongeur according to claim 2 wherein the at least one laterally-extending passageway extends across the complete width of the top shaft.

9. A rongeur according to claim 2 wherein the undercut is formed with square edges.

10. A rongeur according to claim 1 wherein the at least one laterally-extending passageway comprises a longitudinal slit extending vertically through the top shaft and a passageway formed in the at least one side surface of the top shaft.

11. A rongeur according to claim 1 wherein the crossbar is formed with square edges.

12. A rongeur comprising:
  a bottom shaft comprising a proximal end and a distal end, and an upper surface having a groove formed therein, the groove being characterized by a wider proximal recess and a narrower distal recess, the distal end of the bottom shaft terminating in a footplate;
  a top shaft comprising a proximal end and a distal end, at least one side surface disposed between the proximal end and the distal end, and a bottom surface having a tongue projecting downwardly therefrom;
  the bottom surface of the top shaft being slidably disposed on the upper surface of the bottom shaft, and the tongue being slidably disposed in the groove, so that when the top shaft is moved distally relative to the bottom shaft, the tongue slides distally within the groove from the wider proximal recess into the narrower distal recess;
  and at least one laterally-extending passageway formed within the top shaft for admitting air into the portion of the wider proximal recess vacated by the tongue, wherein the at least one passageway opens on the at least one side surface and the bottom surface of the top shaft and is in fluid communication with the groove, wherein the at least one passageway is laterally aligned with at least a portion of the wider proximal recess of the groove in the bottom shaft regardless of the disposition of the top shaft relative to the bottom shaft, whereby to eliminate the potential to generate suction force in the portion of the groove vacated by the tongue as the top shaft moves distally.

13. A rongeur according to claim 12 wherein the tongue sidably disposed in the groove forms a T-slide connection.

14. A rongeur according to claim 12 wherein the at least one laterally-extending passageway is formed in the bottom surface of the top shaft and opens on a side wall of the top shaft.

\* \* \* \* \*